(12) United States Patent
Ujita et al.

(10) Patent No.: US 9,822,085 B2
(45) Date of Patent: Nov. 21, 2017

(54) METHOD FOR PRODUCING TETRAZOLINONE COMPOUND

(71) Applicant: SUMITOMO CHEMICAL COMPANY, LIMITED, Tokyo (JP)

(72) Inventors: Satoru Ujita, Takarazuka (JP); Takayuki Shioda, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/123,353

(22) PCT Filed: Mar. 3, 2015

(86) PCT No.: PCT/JP2015/056763
§ 371 (c)(1),
(2) Date: Sep. 2, 2016

(87) PCT Pub. No.: WO2015/146552
PCT Pub. Date: Oct. 1, 2015

(65) Prior Publication Data
US 2017/0057935 A1 Mar. 2, 2017

(30) Foreign Application Priority Data

Mar. 20, 2014 (JP) .................................. 2014-067940

(51) Int. Cl.
*C07D 257/04* (2006.01)
*C07F 3/02* (2006.01)

(52) U.S. Cl.
CPC .............. *C07D 257/04* (2013.01); *C07F 3/02* (2013.01)

(58) Field of Classification Search
None
See application file for complete search history.

(56) References Cited

U.S. PATENT DOCUMENTS

| 4,868,321 A | 9/1989 | Theodoridis |
| 5,136,868 A | 8/1992 | Theodoridis |

(Continued)

FOREIGN PATENT DOCUMENTS

| EP | 0 708 097 A1 | 4/1996 |
| JP | 61-500069 A | 1/1986 |

(Continued)

OTHER PUBLICATIONS

International Preliminary Report on Patentability and the English translation of the Written Opinion of the International Searching Authority (Forms PCT/IB/373 and PCT/ISA/237), dated Oct. 4, 2016, for International Application No. PCT/JP2015/056763.

(Continued)

*Primary Examiner* — Alicia L Otton
(74) *Attorney, Agent, or Firm* — Birch, Stewart, Kolasch & Birch, LLP

(57) ABSTRACT

A tetrazolinone compound represented by formula (1):

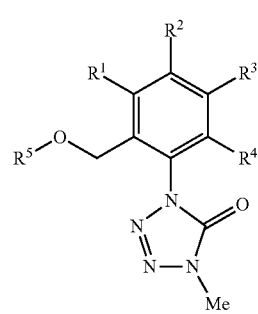

(1)

[in the formula, $R^1$ represents an alkyl group having 1-6 carbon atoms or the like]
can be produced by reacting a compound represented by formula (2):

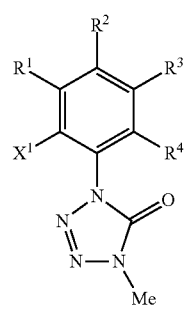

(2)

[in the formula, $X^1$ represents a bromine atom or the like, and $R^1$ represents an alkyl group having 1-6 carbon atoms or the like]
with a compound represented by formula (A):

R—Mg—X    (A)

[in the formula, R represents an alkyl group having 1-6 carbon atoms or the like, and $X^1$ represents a bromine atom or the like]
to provide a compound represented by formula (3):

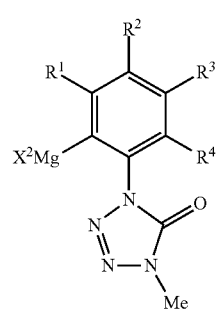

(3)

(Continued)

[in the formula, $X^2$ represents a chlorine atom or the like] and reacting the compound represented by formula (3) with formaldehyde or a compound represented by formula (4):

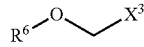

(4)

[in the formula, $R^6$ represents an alkyl group having 1-6 carbon atoms or the like, and $X^3$ represents a chlorine atom, bromine atom or iodine atom].

10 Claims, No Drawings

(56) References Cited

U.S. PATENT DOCUMENTS

| | | | |
|---|---|---|---|
| 5,502,204 A | * | 3/1996 | Yanagi ................. C07D 257/04 544/105 |
| 5,530,135 A | | 6/1996 | Yanagi et al. |
| 6,277,790 B1 | | 8/2001 | Zagar et al. |
| 2004/0102635 A1 | | 5/2004 | Yanagi et al. |
| 2004/0242895 A1 | | 12/2004 | Yanagi et al. |
| 2011/0130415 A1 | | 6/2011 | Singh et al. |

FOREIGN PATENT DOCUMENTS

| | | |
|---|---|---|
| JP | 7-97372 A | 4/1995 |
| JP | 8-119947 A | 5/1996 |
| JP | 2001-114769 A | 4/2001 |
| JP | 2001-512728 A | 4/2013 |
| JP | 2013-512281 A | 4/2013 |
| WO | WO 96/36229 A1 | 11/1996 |
| WO | WO 2013/162072 A1 | 10/2013 |

OTHER PUBLICATIONS

International Search Report, issued in PCT/JP2015/056763, dated May 26, 2015.

* cited by examiner

METHOD FOR PRODUCING TETRAZOLINONE COMPOUND

TECHNICAL FIELD

The present invention relates to a method for producing a tetrazolinone compound.

BACKGROUND ART

WO2013/162072 describes that 1-(2-halogenomethylphenyl)-4-methyl-1,4-dihydrotetrazol-5-ones such as 1-(2-bromomethyl-3-methylphenyl)-4-methyl-1,4-dihydrotetrazol-5-one are useful as a production intermediate of pesticides. Further, as a method for producing 1-(2-bromomethyl-3-methylphenyl)-4-methyl-1,4-dihydrotetrazol-5-one, a production method comprising mixing 1-(2-methoxymethyl-3-methylphenyl)-4-methyl-1,4-dihydrotetrazol-5-one obtained by mixing 1-(2-methoxymethyl-3-bromophenyl)-4-methyl-1,4-dihydrotetrazol-5-one, methylboronic acid and palladium, with hydrogen bromide and acetic acid is described.

SUMMARY OF THE INVENTION

The present invention provides a method for industrially advantageously producing a 1-(2-halogenomethylphenyl)-4-methyl-1,4-dihydrotetrazol-5-one.

The present invention is as described below.

[1] A method for producing a compound represented by formula (1):

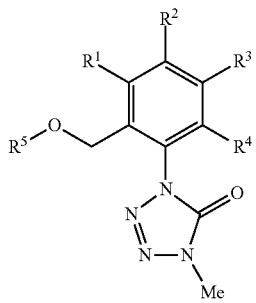

(1)

[wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group]

comprising steps of reacting a compound represented by formula (2):

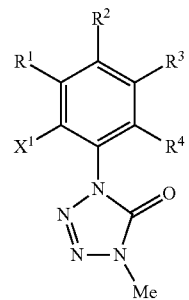

(2)

[wherein $X^1$ represents a bromine atom or an iodine atom, and $R^1$, $R^2$, $R^3$ and $R^4$ have the same meanings as described above]

with a compound represented by formula (A):

$$R-Mg-X \qquad (A)$$

[wherein R represents an alkyl group having 1 to 4 carbon atoms or an aryl group having 6 to 12 carbon atoms, and X represents a chlorine atom, a bromine atom or an iodine atom]

to obtain a compound represented by formula (3):

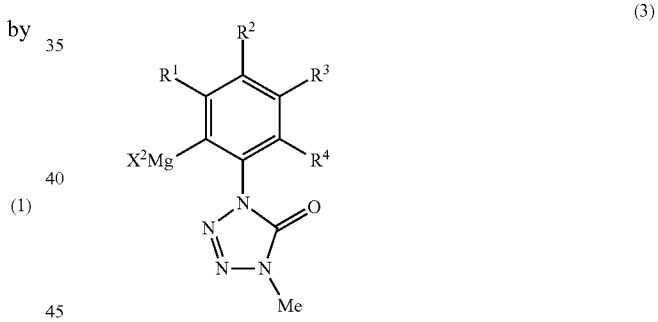

(3)

[wherein $X^2$ represents a chlorine atom, a bromine atom or an iodine atom, and $R^1$, $R^2$, $R^3$ and $R^4$ have the same meanings as described above], and reacting the compound represented by formula (3) with formaldehyde or a compound represented by formula (4):

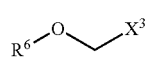

(4)

[wherein $R^6$ represents an alkyl group having 1 to 12 carbon atoms, a phenyl group, a cycloalkyl group having 3 to 6 carbon atoms or an alkenyl group having 2 to 6 carbon atoms, and $X^3$ represents a chlorine atom, a bromine atom or an iodine atom]

to obtain the compound represented by formula (1).

[2] A method for producing a compound represented by formula (1):

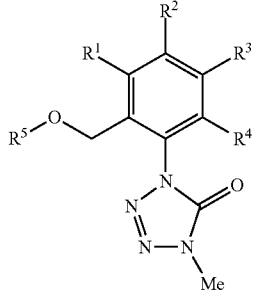

(1)

[wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group]

comprising steps of reacting a compound represented by formula (7)

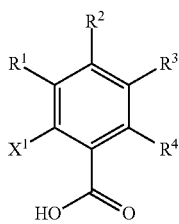

(7)

[wherein $X^1$ represents a bromine atom or an iodine atom, and $R^1$, $R^2$, $R^3$ and $R^4$ have the same meanings as described above]

with a halogenating agent to obtain a compound represented by formula (8):

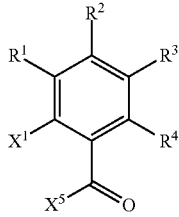

(8)

[wherein $X^5$ represents a chlorine atom or a bromine atom, and $R^1$, $R^2$, $R^3$ and $R^4$ have the same meanings as described above], reacting the compound represented by formula (8) with an azide to obtain a compound represented by formula (11):

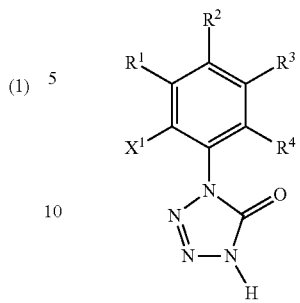

(11)

[wherein $R^1$, $R^2$, $R^3$, $R^4$ and $X^1$ have the same meanings as described above],
reacting the compound represented by formula (11) with a methylating agent to obtain a compound represented by formula (2):

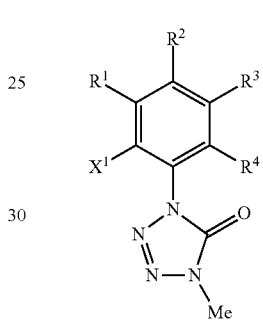

(2)

[wherein $R^1$, $R^2$, $R^3$, $R^4$ and $X^1$ have the same meanings as described above],
reacting the compound represented by formula (2) with a compound represented by formula (A):

R—Mg—X (A)

[wherein R represents an alkyl group having 1 to 4 carbon atoms or an aryl group having 6 to 12 carbon atoms, and X represents a chlorine atom, a bromine atom or an iodine atom]
to obtain a compound represented by formula (3):

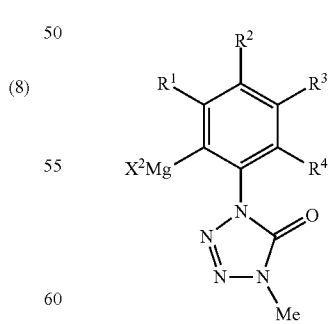

(3)

[wherein $X^2$ represents a chlorine atom, a bromine atom or an iodine atom, and $R^1$, $R^2$, $R^3$ and $R^4$ have the same meanings as described above], and reacting the compound represented by formula (3) with formaldehyde or a compound represented by formula (4)

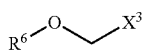
(4)

[wherein $R^6$ represents an alkyl group having 1 to 12 carbon atoms, a cycloalkyl group having 3 to 6 carbon atoms, an alkenyl group having 2 to 6 carbon atoms or a phenyl group, and $X^3$ represents a chlorine atom, a bromine atom or an iodine atom]

to obtain the compound represented by formula (1).

[3] A method for producing a compound represented by formula (5):

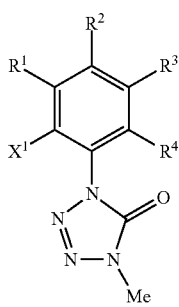
(5)

[wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $X^4$ represents a chlorine atom, a bromine atom or an iodine atom]

comprising steps of reacting a compound represented by formula (2):

(2)

[wherein $X^1$ represents a bromine atom or an iodine atom, and $R^1$, $R^2$, $R^3$ and $R^4$ have the same meanings as described above]

with a compound represented by formula (A):

R—Mg—X  (A)

[wherein R represents an alkyl group having 1 to 4 carbon atoms or an aryl group having 6 to 12 carbon atoms, and X represents a chlorine atom, a bromine atom or an iodine atom]

to obtain a compound represented by formula (3):

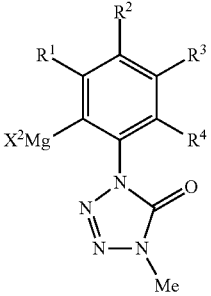
(3)

[wherein $X^2$ represents a chlorine atom, a bromine atom or an iodine atom, and $R^1$, $R^2$, $R^3$ and $R^4$ have the same meanings as described above], reacting the compound represented by formula (3) with formaldehyde or a compound represented by formula (4):

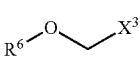
(4)

[wherein $R^6$ represents an alkyl group having 1 to 12 carbon atoms, a cycloalkyl group having 3 to 6 carbon atoms, an alkenyl group having 2 to 6 carbon atoms or a phenyl group, and $X^3$ represents a chlorine atom, a bromine atom or an iodine atom]

to obtain the compound represented by formula (1):

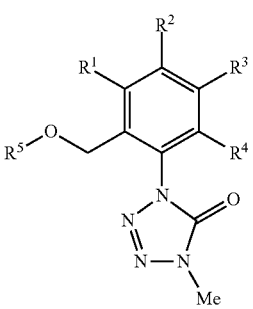
(1)

[wherein $R^1$, $R^2$, $R^3$ and $R^4$ have the same meanings as described above, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group], and reacting the compound represented by formula (1) with hydrogen chloride, hydrogen bromide or hydrogen iodide to obtain the compound represented by formula (5).

[4] A method for producing a compound represented by formula (5):

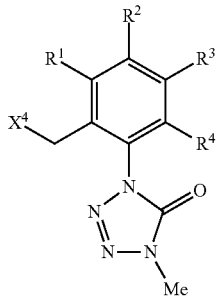
(5)

[wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $X^4$ represents a chlorine atom, a bromine atom or an iodine atom]

comprising steps of reacting a compound represented by formula (7):

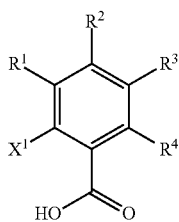
(7)

[wherein $X^1$ represents a bromine atom or an iodine atom, and $R^1$, $R^2$, $R^3$ and $R^4$ have the same meanings as described above]
with a halogenating agent to obtain a compound represented by formula (8):

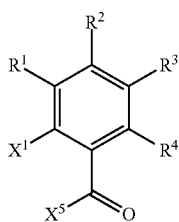
(8)

[wherein $X^5$ represents a chlorine atom or a bromine atom, and $R^1$, $R^2$, $R^3$ and $R^4$ have the same meanings as described above], reacting the compound represented by formula (8) with an azide to obtain a compound represented by formula (11):

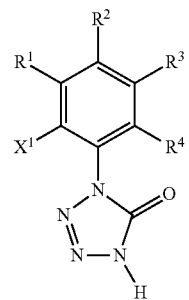
(11)

[wherein $R^1$, $R^2$, $R^3$, $R^4$ and $X^1$ have the same meanings as described above],
reacting the compound represented by formula (11) with a methylating agent to obtain a compound represented by formula (2):

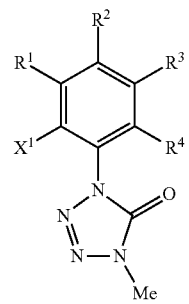
(2)

[wherein $R^1$, $R^2$, $R^3$, $R^4$ and $X^1$ have the same meanings as described above],
reacting the compound represented by formula (2) with a compound represented by formula (A):

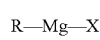

R—Mg—X (A)

[wherein R represents an alkyl group having 1 to 4 carbon atoms or an aryl group having 6 to 12 carbon atoms, and X represents a chlorine atom, a bromine atom or an iodine atom]
to obtain a compound represented by formula (3):

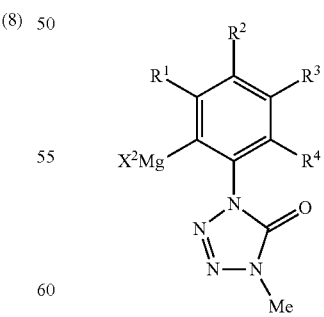
(3)

[wherein $X^2$ represents a chlorine atom, a bromine atom or an iodine atom, and $R^1$, $R^2$, $R^3$ and $R^4$ have the same meanings as described above], reacting the compound represented by formula (3) with formaldehyde or a compound represented by formula (4)

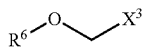
(4)

[wherein $R^6$ represents an alkyl group having 1 to 12 carbon atoms, a cycloalkyl group having 3 to 6 carbon atoms, an alkenyl group having 2 to 6 carbon atoms or a phenyl group, and $X^3$ represents a chlorine atom, a bromine atom or an iodine atom]

to obtain the compound represented by formula (1):

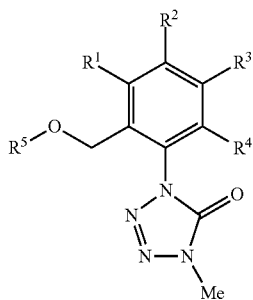
(1)

[wherein $R^1$, $R^2$, $R^3$ and $R^4$ have the same meanings as described above, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group], and reacting the compound represented by formula (1) with hydrogen chloride, hydrogen bromide or hydrogen iodide to obtain the compound represented by formula (5).

[5] A tetrazolinone compound represented by formula (13):

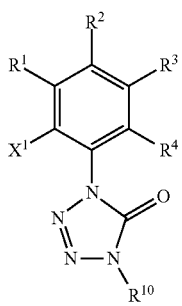
(13)

[wherein $R^{10}$ represents a hydrogen atom or a methyl group, $X^1$ represents a bromine atom or an iodine atom, $R^1$ represents an alkyl group having 1 to 6 carbon atoms or a cycloalkyl group having 3 to 6 carbon atoms, and $R^2$, $R^3$ and $R^4$ each independently represent a hydrogen atom, an alkyl group having 1 to 6 carbon atoms or a cycloalkyl group having 3 to 6 carbon atoms].

[6] A tetrazolinone compound represented by formula (3)

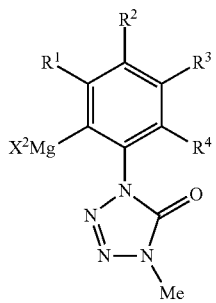
(3)

[wherein $X^2$ represents a chlorine atom, a bromine atom or an iodine atom, $R^1$ represents an alkyl group having 1 to 6 carbon atoms or a cycloalkyl group having 3 to 6 carbon atoms, and $R^2$, $R^3$ and $R^4$ each independently represent a hydrogen atom, an alkyl group having 1 to 6 carbon atoms or a cycloalkyl group having 3 to 6 carbon atoms].

MODE FOR CARRYING OUT THE INVENTION

Examples of the alkyl group having 1 to 6 carbon atoms in $R^1$, $R^2$, $R^3$ and $R^4$ include a methyl group, an ethyl group, a propyl group, an isopropyl group, a butyl group, a sec-butyl group, a tert-butyl group, a pentyl group, and a hexyl group; and alkyl groups having 1 to 3 carbon atoms are preferred.

Examples of the cycloalkyl group having 3 to 6 carbon atoms in $R^1$, $R^2$, $R^3$, $R^4$, $R^5$ and $R^6$ include a cyclopropyl group, a cyclobutyl group, a cyclopentyl group, and a cyclohexyl group; and cycloalkyl groups having 3 to 4 carbon atoms are preferred.

Examples of the alkyl group having 1 to 4 carbon atoms in R include a methyl group, an ethyl group, a propyl group, an isopropyl group, a butyl group, and a tert-butyl group; and alkyl groups having 1 to 3 carbon atoms are preferred.

Examples of the aryl group having 6 to 12 carbon atoms in R include a phenyl group, and a naphthyl group; and a phenyl group is preferred.

Examples of the alkyl group having 1 to 12 carbon atoms in $R^5$ and $R^6$ include a methyl group, an ethyl group, a propyl group, an isopropyl group, a butyl group, a sec-butyl group, a tert-butyl group, a pentyl group, a hexyl group, a nonyl group, a decyl group, an undecyl group, and a dodecyl group; and alkyl groups having 1 to 6 carbon atoms are preferred.

Examples of the alkenyl group having 2 to 6 carbon atoms in $R^5$ and $R^6$ include a vinyl group, an allyl group, a 1-propenyl group, and a 1-methyl-2-propenyl group; and alkenyl groups having 2 to 3 carbon atoms are preferred.

$R^1$ is preferably a methyl group, and $R^2$, $R^3$ and $R^4$ are preferably a hydrogen atom.

$R^5$ is preferably a hydrogen atom and an alkyl group having 1 to 12 carbon atoms, more preferably a hydrogen atom and an alkyl group having 1 to 6 carbon atoms, and particularly preferably a hydrogen atom, a methyl group and an ethyl group.

$R^6$ is preferably an alkyl group having 1 to 12 carbon atoms, more preferably an alkyl group having 1 to 4 carbon atoms, and particularly preferably a methyl group.

Particularly, an embodiment wherein $R^1$ is a methyl group, $R^2$, $R^3$ and $R^4$ are a hydrogen atom, and $R^5$ is a hydrogen atom or a methyl group is preferred.

$X^1$ is preferably a bromine atom, and $X^4$ is preferably a chlorine atom and a bromine atom.

Further, an embodiment wherein $R^1$ is a methyl group, $R^2$, $R^3$ and $R^4$ are a hydrogen atom, and $X^1$ is a bromine atom is preferred.

R is preferably an isopropyl group, and X is preferably a chlorine atom or a bromine atom.

Next, each step will be described in detail.

A compound represented by formula (1) can be produced by steps of reacting a compound represented by formula (2) with a compound represented by formula (A) to obtain a compound represented by formula (3), and reacting the compound represented by formula (3) with formaldehyde or a compound represented by formula (4).

Specific examples of the compound represented by formula (A) include alkylmagnesium chlorides such as methylmagnesium chloride, ethylmagnesium chloride, isopropylmagnesium chloride, butylmagnesium chloride and tert-butylmagnesium chloride; alkylmagnesium bromides such as methylmagnesium bromide, ethylmagnesium bromide, isopropylmagnesium bromide, butylmagnesium bromide and tert-butylmagnesium bromide; alkylmagnesium iodides such as isopropylmagnesium iodide; arylmagnesium chlorides such as phenylmagnesium chloride; arylmagnesium bromides such as phenylmagnesium bromide; and arylmagnesium iodides such as phenylmagnesium iodide. In the compound represented by formula (A), compounds wherein R is an alkyl group having 1 to 4 carbon atoms, and alkylmagnesium chlorides, particularly, isopropylmagnesium chloride is preferred.

As the compound represented by formula (A), a commercially available compound may be used, and the compound can be prepared from an alkyl halide or aryl halide corresponding to magnesium, and the compound prepared in the system may be used.

The use amount of the compound represented by formula (A) is usually from 1 to 10 mol, and preferably from 1 to 3 mol, based on 1 mol of the compound represented by formula (2).

The compound represented by formula (A) may be a compound forming a complex with an inorganic salt such as lithium bromide or lithium chloride.

The reaction of the compound represented by formula (2) with the compound represented by formula (A) is usually performed by mixing both compounds in a solvent. Examples of the solvent include ethers such as tetrahydrofuran, 2-methyltetrahydrofuran, tert-butyl methyl ether, 1,4-dioxane and diethyl ether, hydrocarbons such as heptane, hexane, methylcyclohexane, toluene and xylene, dimethyl sulfoxide, dichloromethane, and chloroform; and preferable are ethers such as tetrahydrofuran and 2-methyltetrahydrofuran.

The compound represented by formula (2) and the compound represented by formula (A) may be mixed at one time, or may be mixed while gradually adding the compound represented by formula (A).

The reaction is carried out usually under an inert gas atmosphere such as nitrogen or argon.

The reaction temperature is usually −80 to 150° C., and preferably −20 to 100° C.

The reaction time is usually 0.1 to 72 hours, and preferably 1 to 24 hours.

The compound represented by formula (3) is usually used in the next step without performing purification operation and isolation operation.

Examples of the compound represented by formula (3) include [2-(4,5-dihydro-4-methyl-5-oxo-1H-tetrazol-1-yl)-6-methylphenyl-1-yl]magnesium chloride, [2-(4,5-dihydro-4-methyl-5-oxo-1H-tetrazol-1-yl)-6-methylphenyl-1-yl]magnesium bromide, [2-(4,5-dihydro-4-methyl-5-oxo-1H-tetrazol-1-yl)-6-methylphenyl-1-yl]magnesium iodide, [2-(4,5-dihydro-4-methyl-5-oxo-1H-tetrazol-1-yl)-6-ethylphenyl-1-yl]magnesium chloride, [2-(4,5-dihydro-4-methyl-5-oxo-1H-tetrazol-1-yl)-6-ethylphenyl-1-yl]magnesium bromide, [2-(4,5-dihydro-4-methyl-5-oxo-1H-tetrazol-1-yl)-6-ethylphenyl-1-yl]magnesium iodide, [2-(4,5-dihydro-4-methyl-5-oxo-1H-tetrazol-1-yl)-6-cyclopropylphenyl-1-yl]magnesium chloride, [2-(4,5-dihydro-4-methyl-5-oxo-1H-tetrazol-1-yl)-6-cyclopropylphenyl-1-yl]magnesium bromide, and [2-(4,5-dihydro-4-methyl-5-oxo-1H-tetrazol-1-yl)-6-cyclopropylphenyl-1-yl]magnesium iodide.

Next, the step of reacting the compound represented by formula (3) with formaldehyde or a compound represented by formula (4) will be described.

Examples of the compound represented by formula (4) include alkoxymethyl derivatives such as methoxymethyl chloride, methoxymethyl bromide, methoxymethyl iodide, ethoxymethyl chloride, ethoxymethyl bromide, ethoxymethyl iodide, hexylmethyl chloride and dodecylmethyl chloride, and aryloxymethyl derivatives such as phenoxymethyl chloride and phenoxymethyl bromide. Alkoxymethyl derivatives are preferred, and methoxymethyl chloride and ethoxymethyl chloride are more preferred.

As the compound represented by formula (4), a commercially available compound may be used, but the compound can be prepared by mixing an alcohol represented by formula (6):

(6)

[wherein $R^6$ has the same meaning as described above] and formaldehyde, in the presence of hydrogen halide such as hydrogen chloride, and the compound prepared in the system may be used.

As formaldehyde, those produced by heating of paraformaldehyde or the like can be used.

The use amount of formaldehyde or the compound represented by formula (4) is usually in a ratio of 1 to 100 mol, and preferably 1 to 10 mol, based on 1 mol of the compound represented by formula (3).

The reaction of the compound represented by formula (3) with formaldehyde or the compound represented by formula (4) is usually performed by mixing both compounds in a solvent, under an inert gas atmosphere such as nitrogen or argon. Examples of the solvent include ethers such as tetrahydrofuran, 2-methyltetrahydrofuran, tert-butyl methyl ether, 1,4-dioxane and diethyl ether, hydrocarbons such as heptane, hexane, methylcyclohexane, toluene and xylene, dimethyl sulfoxide, dichloromethane, and chloroform; and preferable are ethers such as tetrahydrofuran and 2-methyltetrahydrofuran.

The compound represented by formula (3) and formaldehyde or the compound represented by formula (4) may be mixed at one time, or may be mixed while gradually adding formaldehyde or the compound represented by formula (4).

The reaction temperature is usually −80 to 150° C., and preferably −20 to 100° C.

The reaction time is usually 0.1 to 72 hours, and preferably 1 to 24 hours.

The compound represented by formula (1) can be isolated by usual post-treatment such as adding an aqueous solution of an acid, a base or a salt, or a solvent, to the reaction mixture.

Examples of the acid include hydrogen chloride, and sulfuric acid. Examples of the base include sodium hydroxide, potassium hydroxide, sodium carbonate, potassium carbonate, sodium bicarbonate, and ammonia. Examples of the salt include sodium hydrogensulfate, and ammonium chloride. Examples of the solvent include ethyl acetate, toluene, xylene, hexane, heptane, chloroform, dichloromethane, diethyl ether, and tert-butyl methyl ether.

When using a mixture of an aqueous solution of an acid, a base or a salt and a solvent, the concentration of the acid or base is usually 1 to 6 normal, and the concentration of the salt is usually 1 to 6 mol/L. The use amount of the solvent is usually in a ratio of 0.1 to 50 parts by weight, based on 1 part by weight of the compound represented by formula (5).

The isolated compound represented by formula (1) can be purified by washing, chromatography, and the like.

Examples of the compound represented by formula (1) include 1-(2-methoxymethyl-3-methylphenyl)-4-methyl-1,4-dihydrotetrazol-5-one, 1-(2-ethoxymethyl-3-methylphenyl)-4-methyl-1,4-dihydrotetrazol-5-one, 1-(2-propoxymethyl-3-methylphenyl)-4-methyl-1,4-dihydrotetrazol-5-one, 1-(2-isopropoxymethyl-3-methylphenyl)-4-methyl-1,4-dihydrotetrazol-5-one, 1-(2-hexyloxymethyl-3-methylphenyl)-4-methyl-1,4-dihydrotetrazol-5-one, 1-(2-dodecyloxymethyl-3-methylphenyl)-4-methyl-1,4-dihydrotetrazol-5-one, 1-(2-phenoxymethyl-3-methylphenyl)-4-methyl-1,4-dihydrotetrazol-5-one, 1-(2-methoxymethyl-3-ethylphenyl)-4-methyl-1,4-dihydrotetrazol-5-one, 1-(2-ethoxymethyl-3-ethylphenyl)-4-methyl-1,4-dihydrotetrazol-5-one, 1-(2-propoxymethyl-3-ethylphenyl)-4-methyl-1,4-dihydrotetrazol-5-one, 1-(2-isopropoxymethyl-3-ethylphenyl)-4-methyl-1,4-dihydrotetrazol-5-one, 1-(2-hexyloxymethyl-3-ethylphenyl)-4-methyl-1,4-dihydrotetrazol-5-one, 1-(2-dodecyloxymethyl-3-ethylphenyl)-4-methyl-1,4-dihydrotetrazol-5-one, 1-(2-phenoxymethyl-3-ethylphenyl)-4-methyl-1,4-dihydrotetrazol-5-one, 1-(2-methoxymethyl-3-cyclopropylphenyl)-4-methyl-1,4-dihydrotetrazol-5-one, 1-(2-ethoxymethyl-3-cyclopropylphenyl)-4-methyl-1,4-dihydrotetrazol-5-one, 1-(2-propoxymethyl-3-cyclopropylphenyl)-4-methyl-1,4-dihydrotetrazol-5-one, 1-(2-isopropoxymethyl-3-cyclopropylphenyl)-4-methyl-1,4-dihydrotetrazol-5-one, 1-(2-hexyloxymethyl-3-cyclopropylphenyl)-4-methyl-1,4-dihydrotetrazol-5-one, 1-(2-dodecyloxymethyl-3-cyclopropylphenyl)-4-methyl-1,4-dihydrotetrazol-5-one, and 1-(2-phenoxymethyl-3-cyclopropylphenyl)-4-methyl-1,4-dihydrotetrazol-5-one.

Next, the method for producing the compound represented by formula (2) will be described.

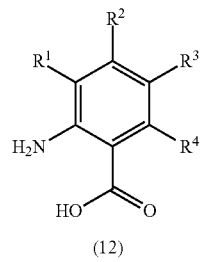

(12)

↓ Diazotizing agent

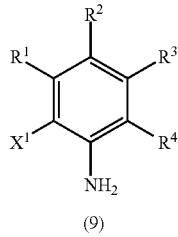

(9)

↓ Phosgenes

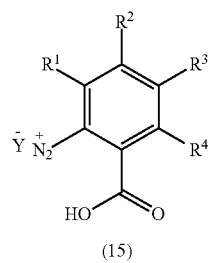

(15)

↓ Halogen or halogen compound

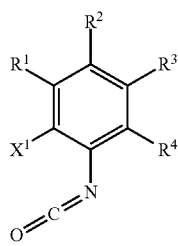

(10)

↓ Azide

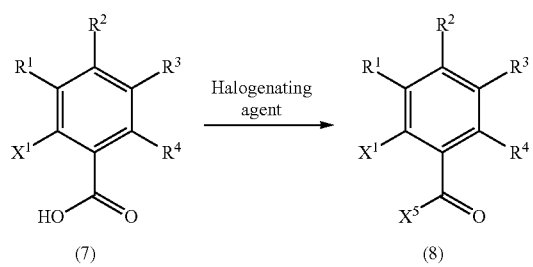
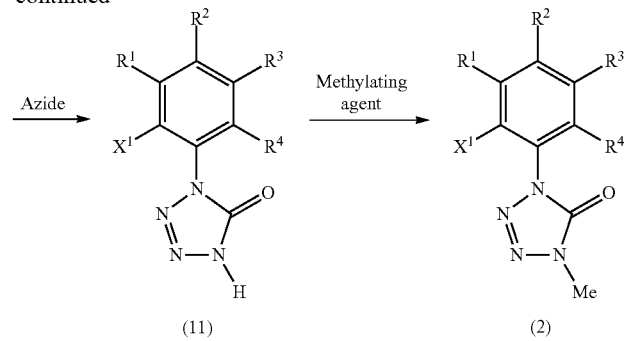

[wherein $Y^-$ represents a counter anion such as halide ion, nitrate ion or sulfate ion, and $R^1$, $R^2$, $R^3$, $R^4$, $X^1$, and $X^5$ have the same meanings as described above].

The compound represented by formula (2) is produced from a compound represented by formula (12) or a compound represented by formula (9). As the compound represented by formula (12) and the compound represented by formula (9), commercially available products are usually used.

A compound represented by formula (15) can be produced by reacting the compound represented by formula (12) with a diazotizing agent.

Examples of the diazotizing agent include nitrites such as sodium nitrite and potassium nitrite. The use amount of the diazotizing agent is usually in a ratio of 0.1 to 50 parts by weight, based on 1 mol of the compound represented by formula (12).

The reaction of the compound represented by formula (12) with the diazotizing agent is usually performed by mixing both compounds in a solvent, in the presence of an acid.

Examples of the acid include hydrochloric acid, sulfuric acid, nitric acid, phosphoric acid, hydrobromic acid, hydriodic acid, acetic acid and trifluoroacetic acid, and mixtures thereof. The use amount of the acid is usually in a ratio of 0.1 to 50 parts by weight, based on 1 part by weight of the compound represented by formula (12).

Examples of the solvent include hydrocarbons such as heptane, hexane, cyclohexane, pentane, toluene and xylene, ethers such as diethyl ether, tetrahydrofuran, 1,4-dioxane, ethylene glycol dimethyl ether, anisole, methyl tert-butyl ether and diisopropyl ether, halogenated hydrocarbons such as carbon tetrachloride, chloroform, dichloromethane, 1,2-dichloroethane, tetrachloroethane and chlorobenzene, esters such as ethyl acetate and methyl acetate, ketones such as acetone, methyl ethyl ketone and methyl isobutyl ketone, nitriles such as acetonitrile and propionitrile, water, and mixtures thereof.

The use amount of the solvent is usually in a ratio of 0.1 to 50 parts by weight, based on 1 part by weight of the compound represented by formula (12).

The reaction may be carried out under a nitrogen atmosphere.

The reaction temperature is usually −20 to 150° C., and preferably −5 to 100° C.

The reaction time is usually 0.1 to 72 hours, and preferably 0.1 to 24 hours.

The obtained compound represented by formula (15) may be subjected to purification operation or isolation operation, but is usually used in the production of a compound represented by formula (7) without purification or isolation.

The compound represented by formula (7) can be produced by reacting the compound represented by formula (15) with halogen or a halogen compound.

The halogen can be bromine, iodine, and the like, and examples of the halogen compound include N-halogenated imides such as N-bromosuccinimide and N-iodosuccinimide, copper halides such as copper bromide and copper iodide, metal halides such as sodium bromide, potassium bromide, sodium iodide and potassium iodide, ammonium halides such as tetrabutylammonium bromide and tetrabutylammonium iodide, alkyl halides such as bromoform, methyl iodide, diiodomethane, ethyl iodide, isopropyl iodide and tert-butyl iodide, hydrogen halides such as hydrogen bromide and hydrogen iodide, iodoalkylsilanes such as iodotrimethylsilane, and haloacetic acids such as iodoacetic acid. Among them, copper bromide is preferably used. The use amount of the halogen or halogen compound is usually from 0.1 to 50 parts by weight, based on 1 part by weight of the compound represented by formula (15).

The reaction may be carried out under a nitrogen atmosphere.

The reaction temperature is usually −20 to 150° C., and preferably −5 to 100° C.

The reaction time is usually 0.1 to 72 hours, and preferably 1 to 24 hours.

The compound represented by formula (7) can be isolated by post-treatment such as adding an aqueous solution of an acid, a base or a salt, or a solvent, to the reaction mixture.

Examples of the acid include hydrogen chloride, and sulfuric acid. Examples of the base include sodium hydroxide, potassium hydroxide, sodium carbonate, potassium carbonate, sodium bicarbonate, and ammonia. Examples of the salt include sodium hydrogensulfate, ammonium chloride, and sodium nitrite. Examples of the solvent include ethyl acetate, toluene, xylene, hexane, heptane, chloroform, dichloromethane, diethyl ether, and tert-butyl methyl ether.

When using a mixture of an aqueous solution of an acid, a base or a salt and a solvent, the concentration of the acid or base is usually 1 to 6 normal, and the concentration of the salt is usually 1 to 6 mol/L. The use amount of the solvent is usually in a ratio of 0.1 to 50 parts by weight, based on 1 part by weight of the compound represented by formula (5).

The isolated compound represented by formula (7) can be purified by washing, chromatography, and the like.

The compound represented by formula (8) can be produced by reacting the compound represented by formula (7) with a halogenating agent.

The reaction of the compound represented by formula (7) with the halogenating agent is usually performed by mixing both compounds in a solvent. Examples of the solvent include hydrocarbons such as heptane, hexane, cyclohexane, pentane, toluene and xylene, ethers such as diethyl ether, tetrahydrofuran, 1,4-dioxane, ethylene glycol dimethyl ether, anisole, methyl tert-butyl ether and diisopropyl ether, halogenated hydrocarbons such as carbon tetrachloride, chloroform, dichloromethane, 1,2-dichloroethane, tetrachloroethane and chlorobenzene, esters such as ethyl acetate and methyl acetate, ketones such as acetone, methyl ethyl ketone and methyl isobutyl ketone, nitriles such as acetonitrile and propionitrile, and mixtures thereof.

The use amount of the solvent is usually in a ratio of 0.1 to 50 parts by weight, based on 1 part by weight of the compound represented by formula (7).

The compound represented by formula (7) and the halogenating agent may be mixed at one time, or may be mixed while gradually adding the halogenating agent.

Examples of the halogenating agent include phosphorus oxychloride, phosphorus trichloride, phosphorus pentachloride, thionyl chloride, phosphorus oxybromide, phosphorus tribromide, phosphorus pentabromide, phosphorus triiodide, oxalyl chloride, oxalyl dibromide, triphosgene, diphosgene, phosgene, and sulfuryl chloride. As the halogenating agent, commercially available products can be used.

The use amount of the halogenating agent is usually in a ratio of 1 to 100 mol, and preferably 1 to 10 mol, based on 1 mol of the compound represented by formula (7).

A catalyst may be added during the mixing, and N,N-dimethylformamide is usually used as the catalyst. The use amount of the catalyst is usually in a ratio of 0.001 to 1 mol, based on 1 mol of the compound represented by formula (7).

The reaction may be carried out under a nitrogen atmosphere.

The reaction temperature is usually −20 to 150° C., and preferably 0 to 100° C.

The reaction time is usually 0.1 to 72 hours, and preferably 1 to 24 hours.

The compound represented by formula (8) can be isolated by concentrating the reaction mixture, and purified by washing, recrystallization, chromatography, and the like, as necessary.

The compound represented by formula (11) can be produced by reacting the compound represented by formula (8) with an azide.

The reaction of the compound represented by formula (8) with the azide is usually performed by mixing both compounds in a solvent. Examples of the solvent include hydrocarbons such as heptane, hexane, cyclohexane, pentane, toluene and xylene, ethers such as diethyl ether, tetrahydrofuran, 1,4-dioxane, ethylene glycol dimethyl ether, anisole, methyl tert-butyl ether and diisopropyl ether, halogenated hydrocarbons such as carbon tetrachloride, chloroform, dichloromethane, 1,2-dichloroethane, tetrachloroethane and chlorobenzene, acid amides such as N,N-dimethylformamide, 1,3-dimethyl-2-imidazolidinone and N-methylpyrrolidone, esters such as ethyl acetate and methyl acetate, sulfoxides such as dimethyl sulfoxide, ketones such as acetone, methyl ethyl ketone and methyl isobutyl ketone, nitriles such as acetonitrile and propionitrile, and mixtures thereof; and ethers such as tetrahydrofuran are preferred.

The use amount of the solvent is usually in a ratio of 0.1 to 50 parts by weight, based on 1 part by weight of the compound represented by formula (8).

The compound represented by formula (8) and the azide may be mixed at one time, or may be mixed while gradually adding the azide.

Examples of the azide include inorganic azides such as sodium azide, barium azide and lithium azide, and organic azides such as trimethylsilyl azide and diphenylphosphoryl azide.

As the azide, commercially available products are usually used.

The use amount of the azide is usually in a ratio of 1 to 100 mol, and preferably 1 to 10 mol, based on 1 mol of the compound represented by formula (8).

It is preferred to add a Lewis acid such as aluminum chloride or zinc chloride during the mixing, and the Lewis acid is usually used in a ratio of 0.05 to 5 mol, based on 1 mol of the compound represented by formula (8).

The reaction may be carried out under a nitrogen atmosphere.

The reaction temperature is usually −20 to 150° C., and preferably 0 to 100° C.

The reaction time is usually 0.1 to 72 hours, and preferably 1 to 24 hours.

The compound represented by formula (11) can be isolated by post-treatment such as adding an aqueous solution of an acid, a base or a salt, or a solvent, to the reaction mixture.

Examples of the acid include hydrogen chloride, and sulfuric acid. Examples of the base include sodium hydroxide, potassium hydroxide, sodium carbonate, potassium carbonate, sodium bicarbonate, and ammonia. Examples of the salt include sodium hydrogensulfate, ammonium chloride, and sodium nitrite. Examples of the solvent include ethyl acetate, toluene, xylene, hexane, heptane, chloroform, dichloromethane, diethyl ether, and tert-butyl methyl ether.

When using a mixture of an aqueous solution of an acid, a base or a salt and a solvent, the concentration of the acid or base is usually 1 to 6 normal, and the concentration of the salt is usually 1 to 6 mol/L. The use amount of the solvent is usually in a ratio of 0.1 to 50 parts by weight, based on 1 part by weight of the compound represented by formula (5).

The isolated compound represented by formula (11) can be purified by washing, chromatography, and the like.

The compound represented by formula (11) can also be produced by reacting the compound represented by formula (10) with an azide. The production method thereof follows the method for producing the compound represented by formula (11) from the compound represented by formula (8).

The compound represented by formula (10) can be produced by reacting the compound represented by formula (9) with phosgenes (phosgene, diphosgene, or triphosgene) according to a conventional method. Specific method is described, for example, in Reference Production Method B of WO2013/162072.

The compound represented by formula (2) can be produced by reacting the compound represented by formula (11) with a methylating agent.

The reaction of the compound represented by formula (11) with the methylating agent is usually performed by mixing both compounds in a solvent. Examples of the solvent include hydrocarbons such as heptane, hexane, cyclohexane, pentane, toluene and xylene, ethers such as diethyl ether, tetrahydrofuran, 1,4-dioxane, ethylene glycol dimethyl ether, anisole, methyl tert-butyl ether and diisopropyl ether, halogenated hydrocarbons such as carbon tetrachloride, chloroform, dichloromethane, 1,2-dichloroethane, tetrachloroethane and chlorobenzene, acid amides such as N,N-dimethylformamide, 1,3-dimethyl-2-imidazolidinone and N-methylpyrrolidone, esters such as ethyl acetate and methyl acetate, sulfoxides such as dimethyl sulfoxide, ketones such as acetone, methyl ethyl ketone and methyl isobutyl ketone, nitriles such as acetonitrile and propionitrile, water, and mixtures thereof. Preferably, the solvent is N,N-dimethylformamide.

The use amount of the solvent is usually in a ratio of 0.1 to 50 parts by weight, based on 1 part by weight of the compound represented by formula (11).

The compound represented by formula (11) and the methylating agent may be mixed at one time, or may be mixed while gradually adding the methylating agent.

Examples of the methylating agent include methyl halides such as methyl bromide and methyl iodide, methyl arylsulfonates such as methyl p-toluenesulfonate, methyl alkylsulfonates such as methyl methanesulfonate, and dimethyl sulfonate.

As the methylating agent, commercially available products can be used.

The use amount of the methylating agent is usually in a ratio of 1 to 100 mol, and preferably 1 to 10 mol, based on 1 mol of the compound represented by formula (11).

During the mixing, a base is preferably added. Examples of the base include organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate, alkali metal hydroxides such as lithium hydroxide, sodium hydroxide, potassium hydroxide and cesium hydroxide, alkali metal hydroxides such as lithium hydroxide, sodium hydroxide and potassium hydroxide, alkali metal hydrides such as lithium hydride, sodium hydride and potassium hydride, and alkali metal alkoxides such as sodium tert-butoxide and potassium tert-butoxide; and potassium carbonate and sodium hydride are preferable. The base is usually used in a ratio of 0.05 to 5 mol, based on 1 mol of the compound represented by formula (11).

The reaction may be carried out under a nitrogen atmosphere.

The reaction temperature is usually −20 to 150° C., and preferably 0 to 100° C.

The reaction time is usually 0.1 to 72 hours, and preferably 1 to 24 hours.

The compound represented by formula (2) can be isolated by post-treatment such as adding an aqueous solution of an acid, a base or a salt, or a solvent, to the mixture.

Examples of the acid include hydrogen chloride, and sulfuric acid. Examples of the base include sodium hydroxide, potassium hydroxide, sodium carbonate, potassium carbonate, sodium bicarbonate, and ammonia. Examples of the salt include sodium hydrogensulfate, ammonium chloride, and sodium nitrite. Examples of the solvent include ethyl acetate, toluene, xylene, hexane, heptane, chloroform, dichloromethane, diethyl ether, and tert-butyl methyl ether.

When using a mixture of an aqueous solution of an acid, a base or a salt and a solvent, the concentration of the acid or base is usually 1 to 6 normal, and the concentration of the salt is usually 1 to 6 mol/L. The use amount of the solvent is usually in a ratio of 0.1 to 50 parts by weight, based on 1 part by weight of the compound represented by formula (5).

The isolated compound represented by formula (2) can be purified by washing, chromatography, and the like.

Examples of the compound represented by formula (2) include 1-(2-bromo-3-methylphenyl)-4-methyl-1,4-dihydrotetrazol-5-one, 1-(2-bromophenyl)-4-methyl-1,4-dihydrotetrazol-5-one, 1-(2-bromo-3-ethylphenyl)-4-methyl-1,4-dihydrotetrazol-5-one, and 1-(2-bromo-3-cyclopropylphenyl)-4-methyl-1,4-dihydrotetrazol-5-one.

Next, the method for producing the compound represented by formula (5) will be described.

The compound represented by formula (5) can be produced by reacting the compound represented by formula (1) with a hydrogen halide (hydrogen chloride, hydrogen bromide, or hydrogen iodide).

The reaction of the compound represented by formula (1) with the hydrogen halide is usually performed by mixing both compounds in a solvent. Examples of the solvent include hydrocarbons such as heptane, hexane, cyclohexane, pentane, toluene and xylene, halogenated hydrocarbons such as carbon tetrachloride, chloroform, dichloromethane, 1,2-dichloroethane, tetrachloroethane and chlorobenzene, ketones such as acetone, methyl ethyl ketone and methyl isobutyl ketone, nitriles such as acetonitrile and propionitrile, organic acids such as formic acid, acetic acid and trifluoroacetic acid, water, and mixtures thereof.

The use amount of the solvent is usually in a ratio of 0.1 to 50 parts by weight, based on 1 part by weight of the compound represented by formula (1).

The hydrogen halide may be used in a gaseous state, or may be used in a state dissolved in an organic solvent or water. The hydrogen halide is preferably used in a state of an aqueous solution or acetic acid solution, and more preferably used in a state of an acetic acid solution.

The compound represented by formula (5) and the hydrogen halide may be mixed at one time, or may be mixed while gradually adding the hydrogen halide.

The use amount of the hydrogen halide is usually in a ratio of 1 to 100 mol, and preferably 1 to 10 mol, based on 1 mol of the compound represented by formula (1).

The reaction may be carried out under a nitrogen atmosphere.

The reaction temperature is usually −20 to 150° C., and preferably 0 to 100° C.

The reaction time is usually 0.1 to 72 hours, and preferably 1 to 24 hours.

The compound represented by formula (5) can be isolated by post-treatment such as adding an aqueous solution of an acid, a base or a salt, or a solvent, to the mixture.

Examples of the acid include hydrogen chloride, and sulfuric acid. Examples of the base include sodium hydroxide, potassium hydroxide, sodium carbonate, potassium carbonate, sodium bicarbonate, and ammonia. Examples of the salt include sodium hydrogensulfate, and ammonium chloride. Examples of the solvent include ethyl acetate, toluene, xylene, hexane, heptane, chloroform, dichloromethane, diethyl ether, and tert-butyl methyl ether.

When using a mixture of an aqueous solution of an acid, a base or a salt and a solvent, the concentration of the acid or base is usually 1 to 6 normal, and the concentration of the salt is usually 1 to 6 mol/L. The use amount of the solvent is usually in a ratio of 0.1 to 50 parts by weight, based on 1 part by weight of the compound represented by formula (5).

The isolated compound represented by formula (5) can be purified by washing, chromatography, and the like.

Examples of the compound represented by formula (5) include 1-(2-chloromethyl-3-methylphenyl)-4-methyl-1,4-dihydrotetrazol-5-one, 1-(2-bromomethyl-3-methylphenyl)-4-methyl-1,4-dihydrotetrazol-5-one, 1-(2-iodomethyl-3-methylphenyl)-4-methyl-1,4-dihydrotetrazol-5-one, 1-(2- chloromethyl-3-ethylphenyl)-4-methyl-1,4-dihydrotetrazol-5-one, 1-(2-bromomethyl-3-ethylphenyl)-4-methyl-1,4-dihydrotetrazol-5-one, 1-(2-iodomethyl-3-ethylphenyl)-4-methyl-1,4-dihydrotetrazol-5-one, 1-(2-chloromethyl-3-cyclopropylphenyl)-4-methyl-1,4-dihydrotetrazol-5-one, 1-(2-bromomethyl-3-cyclopropylphenyl)-4-methyl-1,4-dihydrotetrazol-5-one, and 1-(2-iodomethyl-3-cyclopropylphenyl)-4-methyl-1,4-dihydrotetrazol-5-one.

EXAMPLES

The present invention will be described in further detail below by way of examples.

Example 1

To a mixture of 0.54 g of 1-(2-bromo-3-methylphenyl)-4-methyl-1,4-dihydrotetrazol-5-one obtained in Example 7 described below and 1 mL of tetrahydrofuran was added dropwise 1.69 mL of an isopropylmagnesium chloride-lithium chloride complex tetrahydrofuran solution (concentration of 1.3 mol/L) under ice cooling, and the mixture was stirred under ice cooling for 1 hour. Apart of the reaction mixture was added to hydrochloric acid, and the mixture was extracted with ethyl acetate, and then the organic layer was concentrated. Based on $^1$H-NMR measurement of the concentrated liquid, production of 1-(3-methylphenyl)-4-methyl-1,4-dihydrotetrazol-5-one was confirmed, and thus production of [2-(4,5-dihydro-4-methyl-5-oxo-1H-tetrazol-1-yl)-6-methylphenyl-1-yl]magnesium chloride in the reaction mixture was confirmed.

To the reaction mixture was added 0.18 mL of methoxymethyl chloride and 1 mL of tetrahydrofuran, and the mixture was stirred at 70° C. for 2 hours. Then, saturated saline was added thereto, and the mixture was extracted with ethyl acetate. The organic layer was washed with a saturated sodium bicarbonate aqueous solution and dried over anhydrous sodium sulfate, and then concentrated under reduced pressure to obtain 0.37 g of 1-(2-methoxymethyl-3-methylphenyl)-4-methyl-1,4-dihydrotetrazol-5-one.

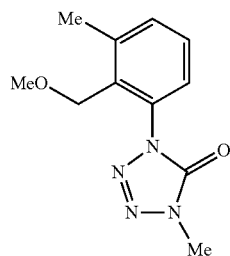 [SMILES: COCc1c(C)cccc1-n1nnn(C)c1=O]

$^1$H-NMR (CDCl$_3$) δ (ppm): 2.48 (3H, s), 3.23 (3H, s), 3.72 (3H, s), 4.42 (2H, s), 7.21 (1H, t, J=5.1 Hz), 7.35 (2H, d, J=4.8 Hz)

Example 2

To a mixture of 0.54 g of 1-(2-bromo-3-methylphenyl)-4-methyl-1,4-dihydrotetrazol-5-one obtained in Example 7 described below and 6 mL of tetrahydrofuran was added dropwise 2.0 mL of an isopropylmagnesium chloride tetrahydrofuran solution (concentration of 2.0 mol/L) under ice cooling, and the mixture was stirred under ice cooling for 1.5 hours. The reaction mixture was sampled and the sample was treated with hydrochloric acid, and then extracted with ethyl acetate and concentrated, and 1-(3-methylphenyl)-4-methyl-1,4-dihydrotetrazol-5-one was confirmed by NMR.

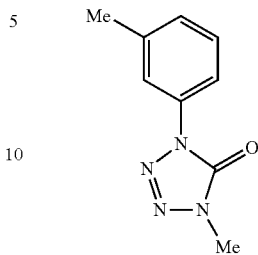

$^1$H-NMR (CDCl$_3$) δ: 3.45 (3H, s), 4.73 (3H, s), 8.20 (1H, d, J=7.8 Hz), 8.40 (1H, t, J=7.8 Hz), 8.76-8.73 (2H, m)

Thereafter, formaldehyde gas generated by heating 1.17 g of paraformaldehyde was blown into the reaction mixture, and saturated saline was added thereto, and then the mixture was extracted with ethyl acetate. The organic layer was washed with a saturated aqueous sodium bicarbonate solution, and dried over anhydrous sodium sulfate. The residue was concentrated under reduced pressure and then purified by a silica gel column to obtain 0.12 g of 1-(2-hydroxymethyl-3-methylphenyl)-4-methyl-1,4-dihydrotetrazol-5-one.

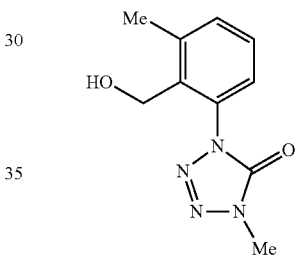

$^1$H-NMR (CDCl$_3$) δ (ppm): 2.56 (3H, s), 3.75 (3H, s), 4.48 (2H, d, J=6.6 Hz), 7.20-7.23 (1H, m), 7.34-7.38 (2H, m)

Example 3

To a mixture of 10.0 g of 1-(2-bromo-3-methylphenyl)-4-methyl-1,4-dihydrotetrazol-5-one obtained in Example 7 described below and 30 mL of tetrahydrofuran was added dropwise 22.3 mL of an isopropylmagnesium chloride tetrahydrofuran solution (concentration of 2.0 mol/L) under ice cooling, and the mixture was stirred under ice cooling for 2.5 hours. To the mixture was added 5.98 g of methoxymethyl chloride, and the mixture was stirred at 70° C. for 3 hours. An aqueous sodium hydrogensulfate solution was added to the mixture, and the resulting mixture was extracted with ethyl acetate. The organic layer was washed with a saturated aqueous sodium bicarbonate solution, and dried over anhydrous sodium sulfate. The residue obtained concentrated under reduced pressure was washed with hexane to obtain 4.5 g of 1-(2-methoxymethyl-3-methylphenyl)-4-methyl-1,4-dihydrotetrazol-5-one.

Example 4

A mixture of 0.25 g of 1-(2-methoxymethyl-3-methylphenyl)-4-methyl-1,4-dihydrotetrazol-5-one obtained in Example 1 and 3 mL of a 25% hydrogen bromide-acetic acid solution was stirred at 65° C. for 1 hour. A saturated saline was added to the mixture, and the resulting mixture was extracted with ethyl acetate. The organic layer was washed with a saturated sodium bicarbonate aqueous solution and dried over anhydrous sodium sulfate, and then concentrated under reduced pressure to obtain 0.23 g of 1-(2-bromomethyl-3-methylphenyl)-4-methyl-1,4-dihydrotetrazol-5-one.

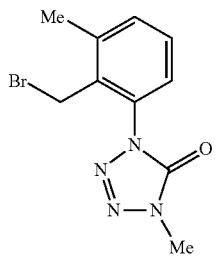 [SMILES: Cc1cccc(-n2nnn(C)c2=O)c1CBr]

$^1$H-NMR (CDCl$_3$) δ (ppm): 2.51 (3H, s), 3.75 (3H, s), 4.51 (2H, s), 7.22-7.24 (1H, m), 7.36-7.39 (2H, m)

Example 5

A mixture of 56 mg of 1-(2-hydroxymethyl-3-methylphenyl)-4-methyl-1,4-dihydrotetrazol-5-one obtained in Example 2, 0.5 mL of acetic acid and 100 mg of a 25% hydrogen bromide-acetic acid solution was stirred at 45° C. for 3 hours, then 200 mg of 25% hydrogen bromide-acetic acid was added thereto, and the mixture was stirred for 5 hours. Water was added to the mixture, and the resulting mixture was extracted with methyl tert-butyl ester. The organic layer was washed with saturated saline, and dried over anhydrous sodium sulfate. The residue was concentrated under reduced pressure, and the resulting residue was purified by a silica gel column to obtain 48 mg of 1-(2-bromomethyl-3-methylphenyl)-4-methyl-1,4-dihydrotetrazol-5-one.

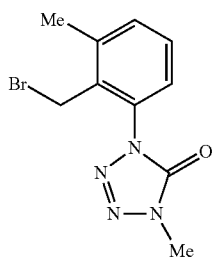 [SMILES: Cc1cccc(-n2nnn(C)c2=O)c1CBr]

$^1$H-NMR (CDCl$_3$) δ (ppm): 2.51 (3H, s), 3.75 (3H, s), 4.51 (2H, s), 7.22-7.24 (1H, m), 7.36-7.38 (2H, m)

Example 6

A mixture of 15.0 g of 2-bromo-3-methylbenzoic acid obtained in Reference Example 1 described below, 9.62 g of oxalyl chloride, 50 mg of N,N-dimethylformamide and 60 g of tetrahydrofuran was stirred at room temperature for 1 hour, then concentrated under reduced pressure, and production of 2-bromo-3-methylbenzoic acid chloride was confirmed by silica gel thin-layer chromatography (developing solvent: hexane/ethyl acetate=5/1, Rf value of 2-bromo-3-methylbenzoic acid chloride: 0.85).

Aluminum chloride (11.16 g) was added to 60 g of tetrahydrofuran under ice cooling, and the mixture was stirred for 30 minutes. Thereto was added 16.46 g of sodium azide, and the mixture was heated and refluxed for 30 minutes, then the whole amount of 2-bromo-3-methylbenzoic acid chloride described above was added, and the mixture was heated and refluxed for 8 hours. After cooling, the reaction liquid was added to a mixture of 17.47 g of sodium nitrite, 100 mL of water and 250 g of ice while stirring the mixture. The mixture was acidified with 10% hydrochloric acid, and then extracted with ethyl acetate. The organic layer was sequentially washed with water and an 10% aqueous sodium hydrogensulfate solution and dried over anhydrous sodium sulfate, and then concentrated under reduced pressure to obtain 16.02 g of 1-(2-bromo-3-methylphenyl)-1,4-dihydrotetrazol-5-one.

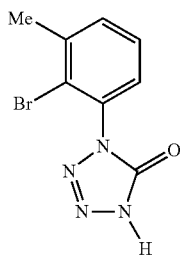 [SMILES: Cc1cccc(-n2nn[nH]c2=O)c1Br]

$^1$H-NMR (CDCl$_3$) δ (ppm): 2.51 (3H, s), 7.27-7.47 (3H, m)

Example 7

A mixture of 14.00 g of 1-(2-bromo-3-methylphenyl)-1,4-dihydrotetrazol-5-one obtained in Example 6, 8.34 g of potassium carbonate, 7.62 g of dimethyl sulfate and 118 mL of N,N-dimethylformamide was stirred at room temperature for 1 hour. Water was added to the mixture, and the resulting mixture was extracted with ethyl acetate. The organic layer was sequentially washed with water and saturated saline and dried over anhydrous magnesium sulfate, and then concentrated under reduced pressure to obtain 9.5 g of 1-(2-bromo-3-methylphenyl)-4-methyl-1,4-dihydrotetrazol-5-one.

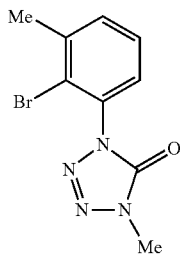 [SMILES: Cc1cccc(-n2nnn(C)c2=O)c1Br]

$^1$H-NMR (CDCl$_3$) δ (ppm): 2.51 (3H, s), 3.73 (3H, s), 7.22-7.41 (3H, m)

Reference Example 1

To a mixture of 1.00 g of 2-amino-3-methylbenzoic acid, 8 mL of acetic acid, 4 mL of 50% hydrobromic acid and 16 mL of water were added 0.46 g of sodium nitrite and 3 mL of water under ice cooling. After stirring the mixture for 10 minutes under ice cooling, disappearance of 2-amino-3-methylbenzoic acid was confirmed by silica gel thin-layer chromatography (developing solvent: hexane/ethyl acetate=1/1, Rf value of 2-amino-3-methylbenzoic acid: 0.67), then 1.42 g of copper bromide and 5 mL of water were added, and the mixture was heated at 50° C. for 3 hours. Water was added to the mixture, and the resulting mixture was filtered to obtain 1.0 g of 2-bromo-3-methylbenzoic acid.

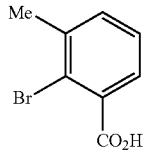

$^1$H-NMR (CDCl$_3$) δ (ppm): 2.49 (3H, s), 7.29 (1H, t, J=7.6 Hz), 7.42 (1H, d, J=7.2 Hz), 7.70 (1H, t, J=3.9 Hz)

INDUSTRIAL APPLICABILITY

According to the present invention, a compound represented by formula (1) can be produced. Further, a compound represented by formula (5) can be produced from the compound represented by formula (1).

The invention claimed is:

1. A method for producing a compound represented by formula (1):

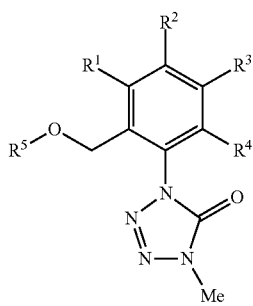

(1)

wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group, comprising steps of reacting a compound represented by formula (2):

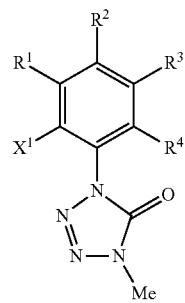

(2)

wherein $X^1$ represents a bromine atom or an iodine atom, and $R^1$, $R^2$, $R^3$ and $R^4$ have the same meanings as described above, with a compound represented by formula (A):

R—Mg—X (A)

wherein R represents an alkyl group having 1 to 4 carbon atoms or an aryl group having 6 to 12 carbon atoms, and X represents a chlorine atom, a bromine atom or an iodine atom, to obtain a compound represented by formula (3):

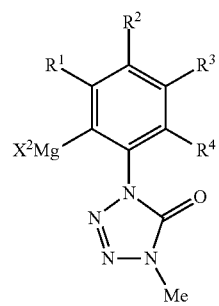

(3)

wherein $X^2$ represents a chlorine atom, a bromine atom or an iodine atom, and $R^1$, $R^2$, $R^3$ and $R^4$ have the same meanings as described above;

and reacting the compound represented by formula (3) with formaldehyde or a compound represented by formula (4):

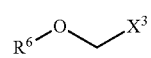

(4)

wherein $R^6$ represents an alkyl group having 1 to 12 carbon atoms, a cycloalkyl group having 3 to 6 carbon atoms, an alkenyl group having 2 to 6 carbon atoms or a phenyl group, and $X^3$ represents a chlorine atom, a bromine atom or an iodine atom, to obtain the compound represented by formula (1).

2. The method according to claim 1, wherein $R^1$ is a methyl group, and $R^2$, $R^3$ and $R^4$ are a hydrogen atom.

3. The method according to claim 1, wherein R is an isopropyl group, and X is a chlorine atom or a bromine atom.

4. A method for producing a compound represented by formula (1):

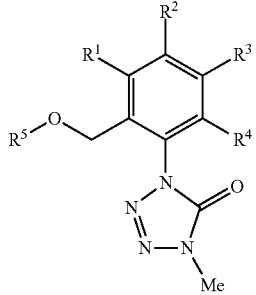
(1)

wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group, comprising steps of reacting a compound represented by formula (7):

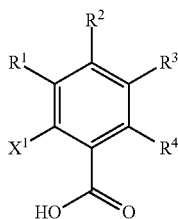
(7)

wherein $X^1$ represents a bromine atom or an iodine atom, and $R^1$, $R^2$, $R^3$ and $R^4$ each independently represent the same meanings as described above, with a halogenating agent to obtain a compound represented by formula (8):

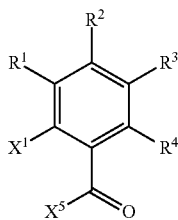
(8)

wherein $X^5$ represents a chlorine atom or a bromine atom, and $R^1$, $R^2$, $R^3$ and $R^4$ have the same meanings as described above;

reacting the compound represented by formula (8) with an azide to obtain a compound represented by formula (11):

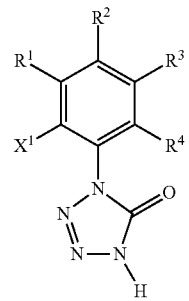
(11)

wherein $R^1$, $R^2$, $R^3$, $R^4$ and $X^1$ have the same meanings as described above;

reacting the compound represented by formula (11) with a methylating agent to obtain a compound represented by formula (2):

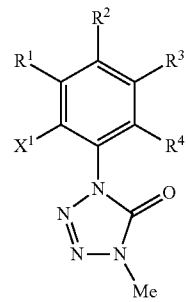
(2)

wherein $R^1$, $R^2$, $R^3$, $R^4$ and $X^1$ have the same meanings as described above;

reacting the compound represented by formula (2) with a compound represented by formula (A):

R—Mg—X  (A)

wherein R represents an alkyl group having 1 to 4 carbon atoms or an aryl group having 6 to 12 carbon atoms, and X represents a chlorine atom, a bromine atom or an iodine atom, to obtain a compound represented by formula (3):

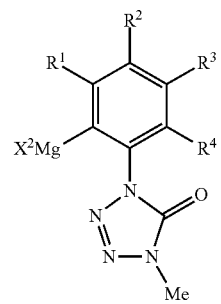
(3)

wherein $X^2$ represents a chlorine atom, a bromine atom or an iodine atom, and $R^1$, $R^2$, $R^3$ and $R^4$ have the same meanings as described above;

and reacting the compound represented by formula (3) with formaldehyde or a compound represented by formula (4):

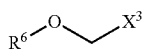
(4)

wherein R⁶ represents an alkyl group having 1 to 12 carbon atoms, a cycloalkyl group having 3 to 6 carbon atoms, an alkenyl group having 2 to 6 carbon atoms or a phenyl group, and X³ represents a chlorine atom, a bromine atom or an iodine atom, to obtain the compound represented by formula (1).

5. The method according to claim 4, wherein R¹ is a methyl group, and R², R³ and R⁴ are a hydrogen atom.

6. The method according to claim 4, wherein R is an isopropyl group, and X is a chlorine atom or a bromine atom.

7. A method for producing a compound represented by formula (5):

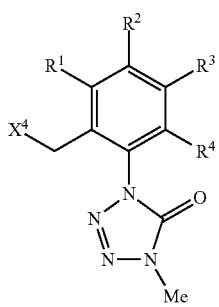
(5)

wherein R¹ represents an alkyl group having 1 to 6 carbon atoms or a cycloalkyl group having 3 to 6 carbon atoms, R², R³ and R⁴ each independently represent a hydrogen atom, an alkyl group having 1 to 6 carbon atoms or a cycloalkyl group having 3 to 6 carbon atoms, and X⁴ represents a chlorine atom, a bromine atom or an iodine atom, comprising steps of reacting a compound represented by formula (2):

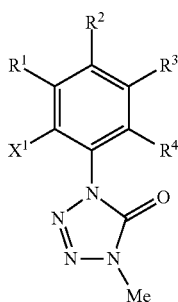
(2)

wherein X¹ represents a bromine atom or an iodine atom, and R¹, R², R³ and R⁴ have the same meanings as described above, with a compound represented by formula (A):

R—Mg—X    (A)

wherein R represents an alkyl group having 1 to 4 carbon atoms or an aryl group having 6 to 12 carbon atoms, and X represents a chlorine atom, a bromine atom or an iodine atom, to obtain a compound represented by formula (3):

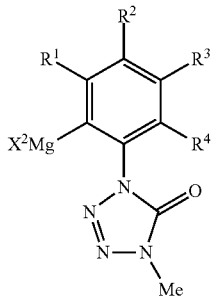
(3)

wherein X² represents a chlorine atom, a bromine atom or an iodine atom, and R¹, R², R³ and R⁴ have the same meanings as described above;

reacting the compound represented by formula (3) with formaldehyde or a compound represented by formula (4):

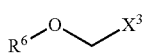
(4)

wherein R⁶ represents an alkyl group having 1 to 12 carbon atoms, a cycloalkyl group having 3 to 6 carbon atoms, an alkenyl group having 2 to 6 carbon atoms or a phenyl group, and X³ represents a chlorine atom, a bromine atom or an iodine atom, to obtain the compound represented by formula (1):

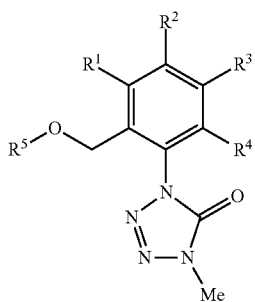
(1)

wherein R¹, R², R³ and R⁴ have the same meanings as described above, and R⁵ represents a hydrogen atom, an alkyl group having 1 to 12 carbon atoms, a cycloalkyl group having 3 to 6 carbon atoms, an alkenyl group having 2 to 6 carbon atoms or a phenyl group;

and reacting the compound represented by formula (1) with hydrogen chloride, hydrogen bromide or hydrogen iodide to obtain the compound represented by formula (5).

8. A method for producing a compound represented by formula (5):

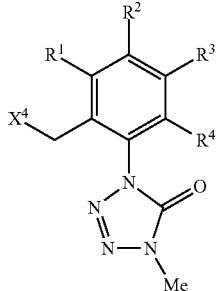

(5)

wherein $R^1$ represents an alkyl group having 1 to 6 carbon atoms or a cycloalkyl group having 3 to 6 carbon atoms, $R^2$, $R^3$ and $R^4$ each independently represent a hydrogen atom, an alkyl group having 1 to 6 carbon atoms or a cycloalkyl group having 3 to 6 carbon atoms, and $X^4$ represents a chlorine atom, a bromine atom or an iodine atom, comprising steps of reacting a compound represented by formula (7):

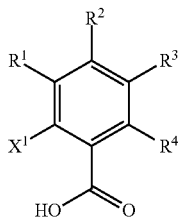

(7)

wherein $X^1$ represents a bromine atom or an iodine atom, and $R^1$, $R^2$, $R^3$ and $R^4$ have the same meanings as described above, with a halogenating agent to obtain a compound represented by formula (8):

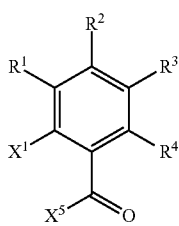

(8)

wherein $X^5$ represents a chlorine atom or a bromine atom, and $R^1$, $R^2$, $R^3$ and $R^4$ have the same meanings as described above;

reacting the compound represented by formula (8) with an azide to obtain a compound represented by formula (11):

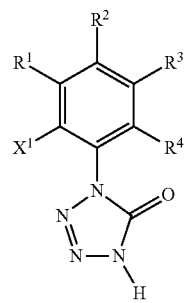

(11)

wherein $R^1$, $R^2$, $R^3$, $R^4$ and $X^1$ have the same meanings as described above;

reacting the compound represented by formula (11) with a methylating agent to obtain a compound represented by formula (2):

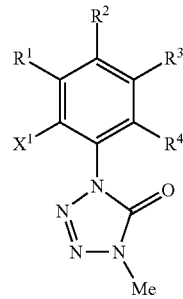

(2)

wherein $R^1$, $R^2$, $R^3$, $R^4$ and $X^1$ have the same meanings as described above;

reacting the compound represented by formula (2) with a compound represented by formula (A):

R—Mg—X    (A)

wherein R represents an alkyl group having 1 to 4 carbon atoms or an aryl group having 6 to 12 carbon atoms, and X represents a chlorine atom, a bromine atom or an iodine atom, to obtain a compound represented by formula (3):

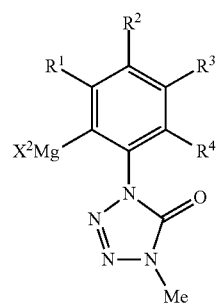

(3)

wherein $X^2$ represents a chlorine atom, a bromine atom or an iodine atom, and $R^1$, $R^2$, $R^3$ and $R^4$ have the same meanings as described above;

reacting the compound represented by formula (3) with formaldehyde or a compound represented by formula (4):

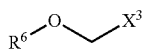 (4)

wherein $R^6$ represents an alkyl group having 1 to 12 carbon atoms, a cycloalkyl group having 3 to 6 carbon atoms, an alkenyl group having 2 to 6 carbon atoms or a phenyl group, and $X^3$ represents a chlorine atom, a bromine atom or an iodine atom, to obtain the compound represented by formula (1):

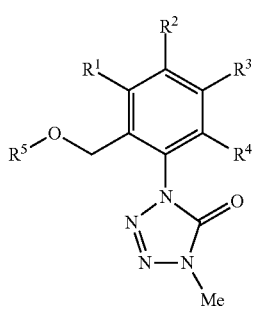 (1)

wherein $R^1$, $R^2$, $R^3$ and $R^4$ have the same meanings as described above, and $R^5$ represents a hydrogen atom, an alkyl group having 1 to 12 carbon atoms, a cycloalkyl group having 3 to 6 carbon atoms, an alkenyl group having 2 to 6 carbon atoms or a phenyl group;

and reacting the compound represented by formula (1) with hydrogen chloride, hydrogen bromide or hydrogen iodide to obtain the compound represented by formula (5).

9. A tetrazolinone compound represented by formula (13):

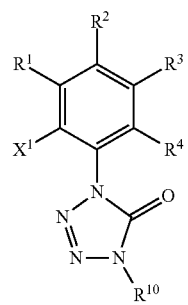 (13)

wherein $R^{10}$ represents a methyl group, $X^1$ represents a bromine atom or an iodine atom, $R^1$ represents an alkyl group having 1 to 6 carbon atoms or a cycloalkyl group having 3 to 6 carbon atoms, and $R^2$, $R^3$ and $R^4$ each independently represent a hydrogen atom, an alkyl group having 1 to 6 carbon atoms or a cycloalkyl group having 3 to 6 carbon atoms.

10. A tetrazolinone compound represented by formula (3):

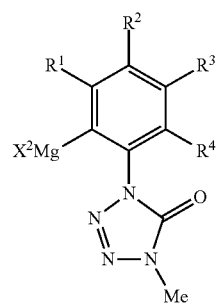 (3)

wherein $X^2$ represents a chlorine atom, a bromine atom or an iodine atom, $R^1$ represents an alkyl group having 1 to 6 carbon atoms or a cycloalkyl group having 3 to 6 carbon atoms, and $R^2$, $R^3$ and $R^4$ each independently represent a hydrogen atom, an alkyl group having 1 to 6 carbon atoms or a cycloalkyl group having 3 to 6 carbon atoms.

* * * * *